United States Patent [19]

Power

[11] 3,986,505
[45] Oct. 19, 1976

[54] EMERGENCY BURN TREATMENT PACK

[76] Inventor: Ronald A. Power, 2110 230th St., Torrance, Calif. 90501

[22] Filed: Aug. 1, 1975

[21] Appl. No.: 600,938

[52] U.S. Cl. .......................... 128/132 R; 128/157; 128/268; 5/82 R; 5/89; 206/440; 128/149
[51] Int. Cl.² ...................... A61F 13/00; E03D 5/04
[58] Field of Search ........................... 128/155–156, 128/157, 268, 149, 132 R, 132 D, DIG. 24; 5/82, 89; 206/440

[56] References Cited
UNITED STATES PATENTS

| | | | |
|---|---|---|---|
| 2,279,694 | 4/1942 | Martinson | 5/82 |
| 2,600,501 | 6/1952 | Higgs | 5/89 X |
| 3,361,132 | 1/1968 | Rentsch | 128/134 |
| 3,648,291 | 3/1972 | Pankers | 128/149 |
| 3,708,810 | 1/1973 | Merikallio | 5/82 |
| 3,734,058 | 5/1973 | Hightower et al. | 5/82 X |

*Primary Examiner*—Lawrence W. Trapp
*Attorney, Agent, or Firm*—Singer & Singer

[57] ABSTRACT

A first aid package for emergency use in the field for treating and transporting seriously burned patients. The first aid package comprises a soft resilient water absorbent foam material placed on a flexible waterproof outer covering having a pair of interlocking portions. A sterile sheet is placed over the resilient foam material and the sheet and the foam are saturated with an aqueous solution. The burn patient is placed on the sterile sheet and completely covered by the sterile sheet thereby enclosing the patient in a sterile atmosphere. An aqueous solution is then poured over the sheet so as to completely saturate the sheet and the uppermost portion of the patient. The cooperating interlocking portions of the flexible waterproof covering are placed completely around the sheet and the patient and locked into position thereby maintaining the patient in a sterile moist atmosphere. Openings are provided in the waterproof covering to provide access to the patient's arms and legs for intravenous blood transfusions should that be necessary. A pair of flexible straps located on each side of the waterproof outer covering provide the means for transporting the patient while in the sterile and moist protective cocoon environment.

12 Claims, 7 Drawing Figures

EMERGENCY BURN TREATMENT PACK

This invention is concerned with an apparatus and method of providing emergency treatment to burn patients in the field.

The treatment of burn patients in a hospital is concerned primarily with keeping the patient comfortable, keeping the patient cool, and providing a sterile atmosphere about the patient.

It is well known that burn patients with third degree burns on the major portions of their body suffer primarily from infection caused by non-sterile materials contacting the open flesh and by the loss of fluids from their body as the result of lost skin.

Unfortunately the treatment of burn patients in the field, defined as the place of the holocaust, is at best haphazard and results directly from the lack of equipment and method for treating the burn patient, protecting him from infection and then transporting him to the hospital for final treatment by attending physicians.

In most towns and cities the first semi-professional people to arrive at the scene of an accident, fire or holocaust are either paramedics associated with the fire department, police department, or ambulance teams. The accepted procedure today for treating a burn patient is to cover the patient with a sterilized sheet and wet him down with an aqueous solution.

Unfortunately, treating a fire fighter at the scene of a forest fire in a forest does not provide any procedure for covering the patient and pouring water over him. For example, simply putting a sheet over the patient and pouring water over him and then rolling him over to treat him on the back does nothing but create a mud puddle about the patient.

In addition, the water solution simply rolls off the patient onto the ground which does nothing to help cool the patient but creates additional problems with respect to cleanliness and contamination of the burned areas.

The present invention is concerned primarily with providing an apparatus for holding a patient in a sterile atmosphere capable of being moistened and at the same time provide a means of transporting the patient while he is maintained in the sterile moist environment.

The burn package and the method described in this invention is capable of being used by semi-skilled personnel and not only provides a means of maintaining the patient in a sterile atmosphere but also provides for his genuine comfort while he is transported from the scene to the hospital for final treatment.

There is absolutely no procedure or method available today that is capable of providing for the burned patient's comfort while he is transported from the accident scene to the hospital.

In this invention there is described a resilient water absorbent foam material having the thickness of at least 1 inch for supporting a patient. The foam material is placed over a waterproof outer covering having extended arms capable of interlocking with each other so as to completely encompass a patient placed on the foam material.

In the practice of the invention, a sterile sheet of the type usually supplied in a sterilized container is opened and placed in a closed position on the foam material. At this point an aqueous solution is used to completely wet down the sheet and the foam material. The waterproof outer covering, being waterproof, will hold the saline solution and prevent the solution from leaving the area of the foam rubber.

The patient is placed on the sterilized sheet which immediately places his back portion in contact with the sheet and the foam material that is saturated in the aqueous solution thereby providing instant relief and cooling to the back portion of his body including his arms and his legs wherever his body has been burned.

The paramedic then places saturated sterile towels and saturated gauze over the patient's head and other parts of his body while the patient is lying on the sterilized sheet. The sterilized sheet is then opened and placed around the patient's body so as to completely cover all portions of his body thereby effectively sealing the patient's body within the confines of the sterilized sheet in an effort to reduce the chances of infection to a minimum.

An aqueous solution is then used to completely wet the sterilzed sheet on the top side of the patient thereby cooling the patient on the upper part of his body which also tends to keep the sterilized sheet in place.

The overlapping interlocking portions of the waterproof covering are located completely around the patient and locked in position preferably with Velco fasteners located transversely of the patient so as to completely enclose the patient and hold the sterilized sheet in position.

In this manner the patient is completely enclosed in a moist sterile environment with all parts of his body completely covered by the sterile sheet and the liquid solution is maintained within the confines of the waterproof container.

In the preferred embodiment the waterproof container contains a pair of flexible handles on each side to provide a convenient means for transporting the patient while he is maintained within the sterile moist environment. Since the outer waterproof container is flexible, it is a simple matter to vary the body position of the patient which may be necessary since many burn patients suffer pulmonary congested heart failure due to pulmonary adema in the lungs. The flexibility of the carrying mechanism provides a convenient means of elevating the head of the patient without touching the patient and without fear that the liquid within the waterproof container will run out.

Certain modifications which include ports located on each side of the patient's arm and leg portions in the waterproof container provide a means of accessing the patient's arms and legs to provide intravenous feeding and blood transfusions should that be necessary without completely exposing the patient to external bacteria in the atmosphere.

Further objects and advantages of the present invention will be made more apparent by referring now to the accompanying drawings wherein.

The described method and apparatus may be used for any preferred treatment of the burn patient since it is conceivable that a dry sterile environment may in certain situations be considered more desirable than a moist sterile environment. In either case the cocoon arrangement described herein is equally adaptable for either preferred procedure.

Figure 1:
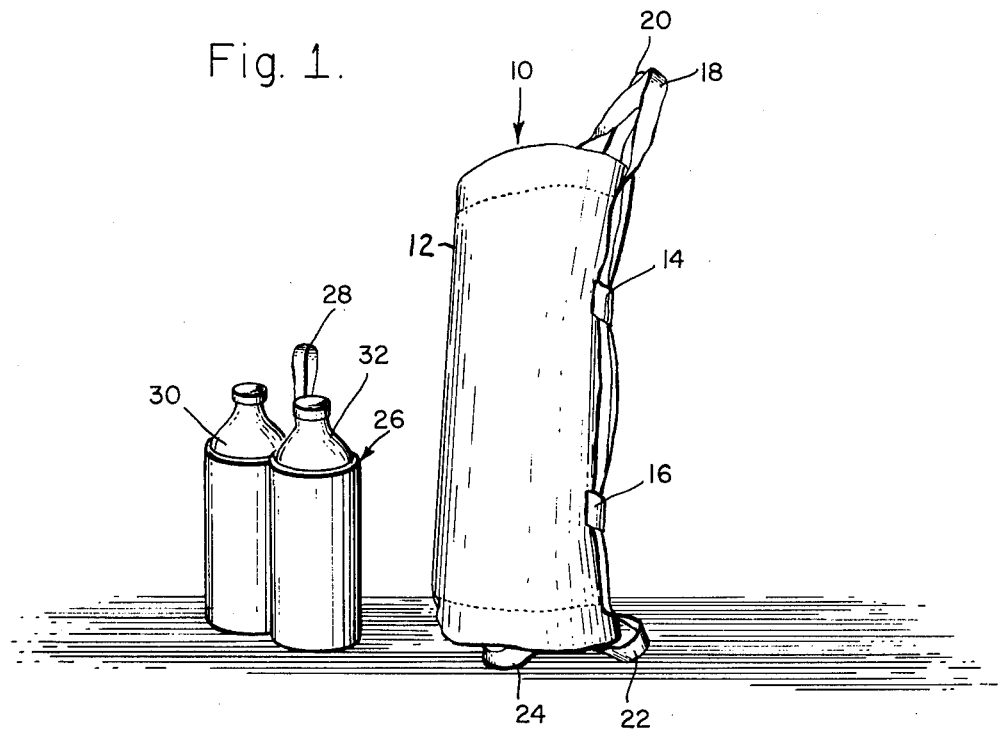
FIG. 1 illustrates a perspective view of the emergency burn treatment package in a stored position.

Referring now to FIG. 1, there is shown an emergency burn treatment package 10 having an outer package 12 consisting of a flexible waterproof material rolled together and held in a tightly closed position by means of a pair of Velco fasteners 14 and 16. A pair of carrying straps 18, 20 and 22 and 24 are located on each side of the burn package 10 in order to facilitate holding and moving the burn package and also serve as a means of carrying the patient as is disclosed and illustrated in connection with FIG. 7.

According to the present state-of-the-art for treating burn patients, it is considered most desirable to keep the patient in a moist condition and there is included a fabric container 26 having an appropriate handle 28 and adapted to hold two sterilized bottles 30 and 32 each containing a given amount of sterilized aqueous solution. The burn package 10 and the fabric container 26 are usually in close proximity to each other so as to be ready and available for immediate use as the need dictates.

The construction and the use of the burn package 10 will be described simultaneously in connection with FIGS. 2 through 7.

Figure 2:
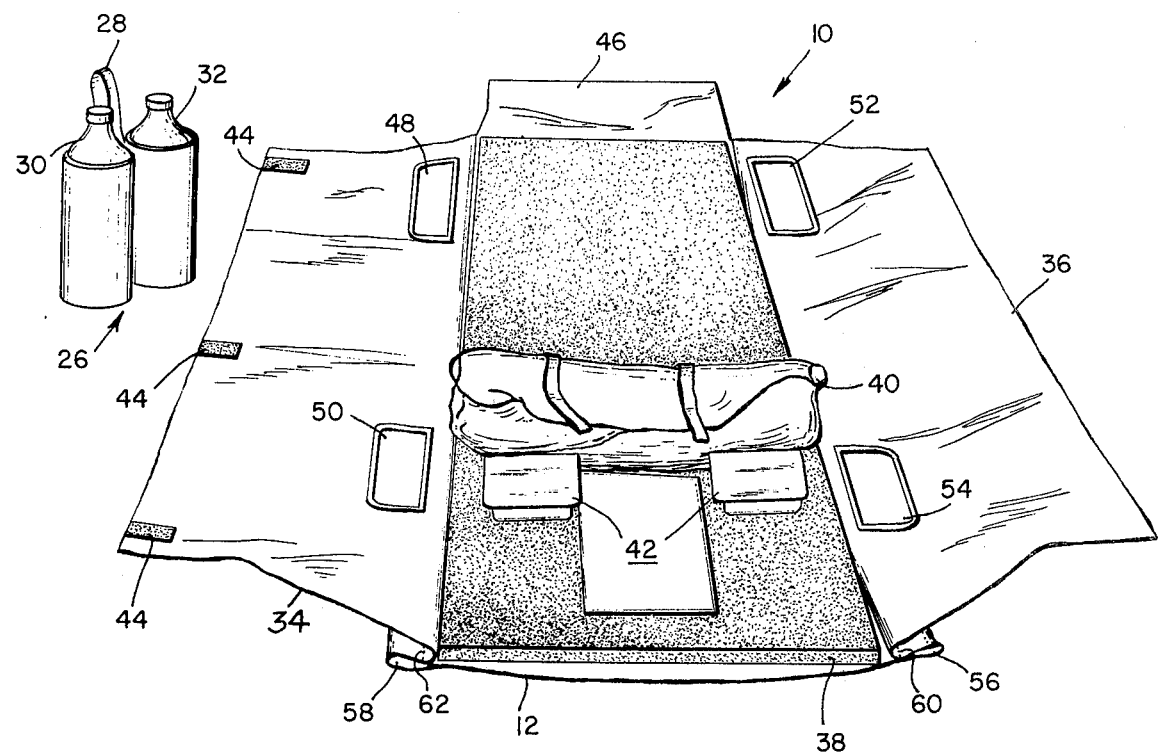
FIG. 2 illustrates a perspective view of the emergency burn package with the waterproof flap portions in an opened position.

Referring now to FIG. 2, there is shown the burn package 10 consisting of the outer waterproof material 12 having a pair of cooperating interlocking portions 34 and 36.

Located on the centralmost portion of the outer covering 12 is a soft resilient water absorbent material 38 preferably constructed of foam having the thickness of at least one to two inches thick sufficient to support the body of a patient.

Located on the foam material 38 is a standard sterilized package 40 containing sterilized sheets and sterilized towels which will be used to cover the patient after he is located on the foam material 38. Also located within the burn package 10 are sterilized packages 42 which contain sterilized gauze of different sizes and thicknesses for use in treating the patient.

The burn package 10 is adapted to receive an aqueous solution and to hold the solution within the confines of the outer covering 12 while the patient is moved from the place of the injury to the hospital.

Overlapping portions 34 and 36 contain Velco fastenings 44 located on the bottommost side of overlapping portion 34 so as to mate with Velco fastenings located on the uppermost side of flap portion 36 thereby allowing overlapping portions 34 and 36 to completely encompass a patient lying on the foam material 38.

An additional flap 46 constructed of the same outerproof covering as 12, 34 and 36 is formed at the end portion of the outer covering 12 and is adapted to fold over the foam material so as to prevent fluid absorbed by the foam material 38 from leaving the confines of the enclosure.

In the preferred embodiment the outer covering 12 and the overlapping portions 34 and 36 and flap 46 are preferably constructed from a single piece of material in order to enhance the ability of the waterproof material to hold the moisture and to provide additional strength in carrying the patient.

Overlapping flap 34 contains a pair of small flap openings 48 and 50 located relatively close to the edge of the foam material in order to provide access from the outside to the patient's left foot by means of flap 48 and the patient's left hand by means of flap 50. In a similar manner, overlapping portion 36 contains a small flap opening 52 and 54 also located close to the foam mattress but on the other side so as to provide access to the patient's right foot through flap 52 and the patient's right arm through flap 54. The application of flaps 48, 50, 52 and 54 is more fully illustrated in connection with FIG. 6 which illustrates how the patient may be completely enclosed within the burn package 10 and still make his arms and legs available either for intravenous feeding and/or blood transfusions should that be necessary and without removing the patient from his sterile moist enclosure.

Figure 6:
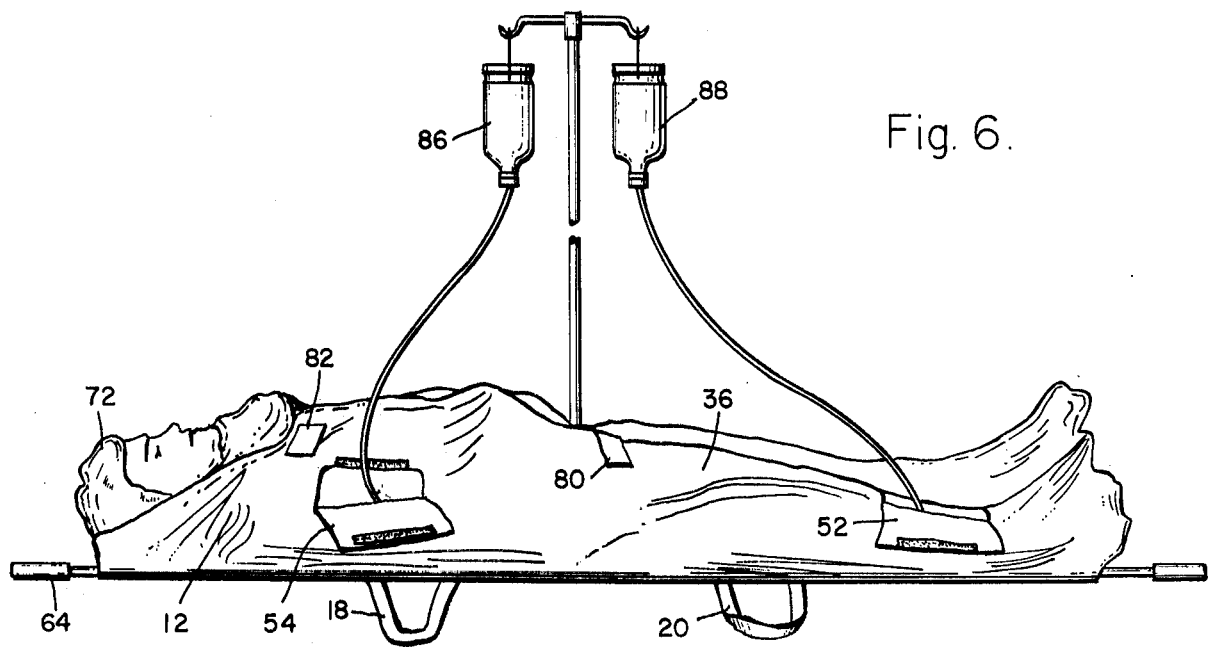
FIG. 6 illustrates how the burn patient can receive intravenous treatment and blood transfusions while maintained within this moist sterile atmosphere.

The burn package 10 also provides optional means for carrying the patient while the patient is held within the confines of the burn package. The outer waterproof covering 12 is looped on each side of the foam material as at 56 and 58 and stitched as at 60 and 62. Both loops 56 and 58 extend lengthwise and parallel with the edge of the foam material and provide means for each accepting a pole 64 as is more fully illustrated in connection with FIG. 6. FIG. 6 also illustrates the optional handles 18 and 20 located on one side of the outer covering 12 for carrying the patient. Handles 22 and 24 shown in FIG. 1 are located on the other side thereby allowing two men or a man on each handle to carry the patient while he is encompassed in the moist and sterile atmosphere.

Figure 3:
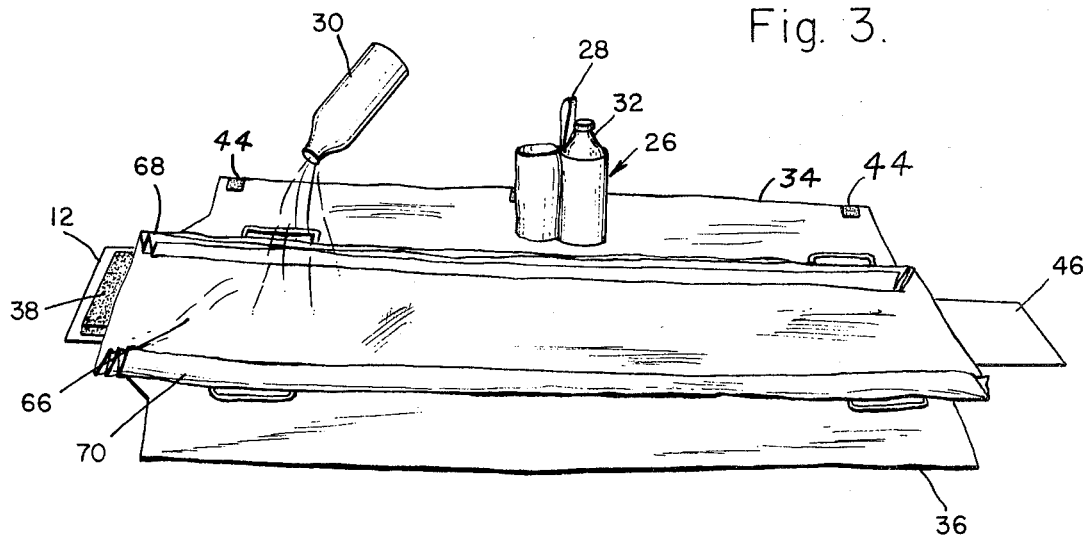
FIG. 3 illustrates the emergency burn treatment package with the sterilized sheet placed on the foam material being saturated with an aqueous solution.

Referring now to FIG. 3, there is shown burn package 10 in an open position. In the position shown in FIG. 3 the sterilized package 40 has been opened and a sterilized sheet 66 has been placed over the foam material 38 in such a manner that the edge portions 68 and 70 of the sheet are still in a folded position extending lengthwise the foam mattress 38.

In this position the aqueous solution from one of the bottles 30 is poured on the sheet so as to saturate both the sheet 66 and the foam mattress 38.

Figure 4:
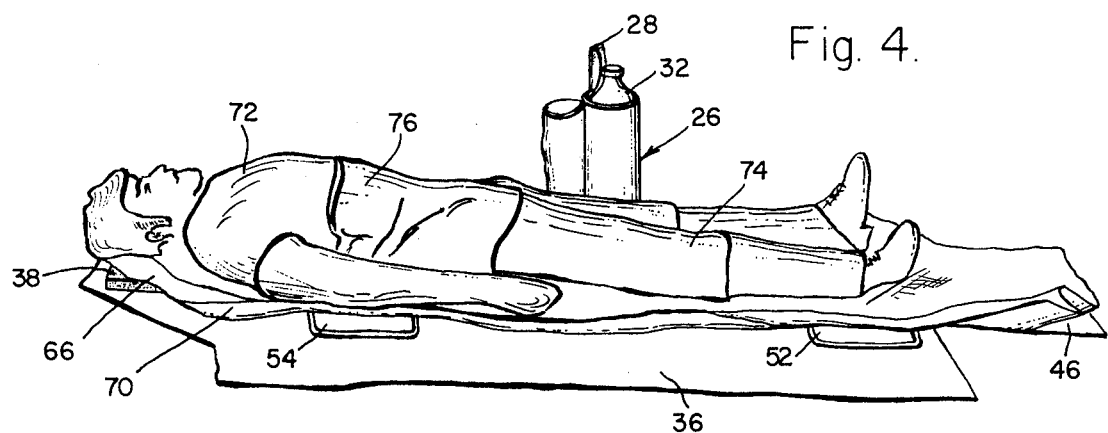
FIG. 4 illustrates a burn patient having saturated gauzes and towels placed on his body as he lies on the saturated sterile sheet.

Referring now to FIG. 4 there is shown a burn patient 72 lying on the saturated sheet 66 and foam mattress 38. In this illustration individual sterilized towels 74 and sterilized gauzes 76 have been placed on the patient and moistened by the aqueous solution from bottles 30 or 32.

Figure 5:
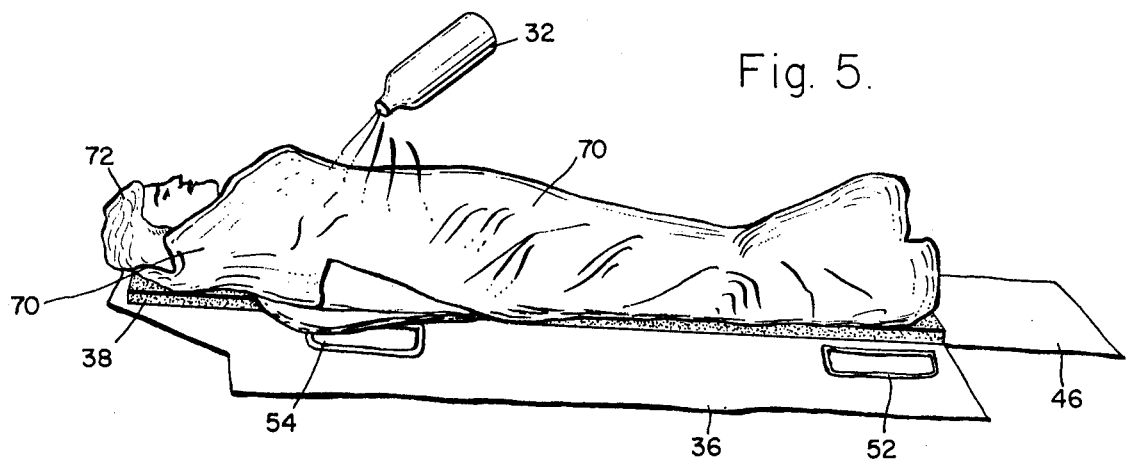
FIG. 5 illustrates the burn patient completely covered by the sterile sheet being saturated with an aqueous solution.

Referring now to FIG. 5 there is shown how the end portions 70 of the sterilized sheet have been placed over and around the patient 72. In a similar fashion the other edge 68 of the sterilized sheet has been unfolded and placed around the patient 72 so as to completely encompass the patient and prevent exposure of any exposed tissues to the atmosphere.

Referring now to FIG. 5 there is shown how the remaining aqueous solution from bottle 32 is now poured over the top portion of the patient 72 so as to saturate the unfolded portion 68 and the unfolded portion 70 of the sterilized sheet 66 which is now completely encompassing the patient. The remaining liquid from bottle 32 is absorbed by the sterilized sheet, sterilized gauze and sterilized toweling in contact with the patient. In this configuration the patient is now in a cool state and all exposed parts of his body are covered by sterilized materials.

Referring now to FIG. 6 there is shown how the patient is completely enclosed by means of the outer waterproof covering 12. In order to prevent liquid within the container from escaping, flap 46 is first folded over the patient's legs on top of the sterile sheet 66. The cooperating interlocking portions 34 and 36 then completely enclose the patient and are interlocked together by means of the Velco fasteners 44 and 80. In this fashion the patient 72 is completely enclosed within the confines of the outer waterproof material 12 in such a manner that the liquid is prevented from escaping and the patient is at all times contacted only by moist sterile garments.

FIG. 6 also illustrates how intravenous connections may be made to supply fluid to the arms of the patient through, for example, flap 52 by means of bottle 86 or how blood transfusions may be made to the victim's feet through flap 54 by means of bottle 88. Should intravenous feeding or blood transfusions be necessary, it is only necessary to open the individual flap whether it be 48, 50, 52 or 54, depending upon the treatment being afforded the patient. At all other times the individual flap will be closed thereby ensuring that the patient is maintained in his cool sterile environment.

FIG. 6 also illustrates how two poles 64 may be used to carry the patient using the outer waterproof covering 12 as the carrying vehicle without disturbing the moist sterile environment in which the patient is residing.

In the treatment of burn patients it is always necessary to check the pulse and the artery on the jugular veins since it is possible that the veins may start puffing due to pulmonary congested heart failure due to pulmonary adema in the lungs. This situation creates great difficulty in the patient to breathe and it is immediately necessary to make the patient comfortable by tilting his torso into a sitting position in order to help the breathing process.

Figure 7:
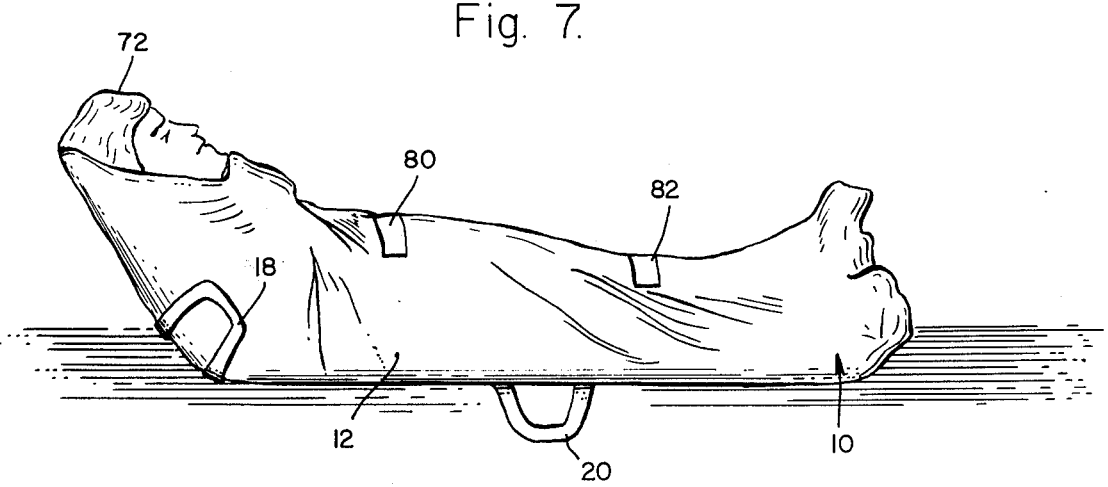
FIG. 7 illustrates the burn patient completely encompassed within the flexible waterproof outer garment having the upper portions of his body raised without upsetting this moist sterile environment.

Referring now to FIG. 7 there is shown an illustration of how the patient 72 located within the confines of the outer waterproof covering 12 is able to be maneuvered and positioned into a sitting position without disturbing the sterile moist environment in which the patient is placed. The flexibility of the burn package 10 allows the patient to be manipulated and carried without the necessity of having to remove him from a stretcher or other fixed device which is the usual case in transporting patients.

It will be appreciated by those skilled in the art that the defined burn package may be used either in a moist or in a dry mode, however, it will be appreciated that the structure is particularly adaptable to a moist atmosphere since it is now possible to maintain the moist atmosphere within the confines of the sterile environment in which the patient is placed in at the scene of the catastrophe.

I claim:

1. An emergency burn treatment package for maintaining the patient in a sterile moist atmosphere comprising:
   a soft resilient water absorbent foam material for holding liquid in suspension and adapted to support a patient lying on said foam material,
   an absorbent sterile sheet on said foam material interspersed between said foam material and a patient lying on said material and adapted to completely cover and protect said patient from contamination, and
   a flexible waterproof outer covering having at least a pair of cooperating interlocking portions completely encompassing said foam material, patient and said sterile sheet for maintaining a moist condition about the patient.

2. An emergency burn package according to claim 1 in which said pair of cooperating portions include a plurality of transverse fasteners for interlocking said portions over a wide range of body sizes.

3. An emergency burn package according to claim 2 in which said plurality of transverse fasteners comprise individual Velco fasteners for fastening said cooperating portions in a plurality of different positions.

4. An emergency burn package according to claim 1 in which each cooperating portion has a pair of flap openings for providing access to either hand or foot of the patient should external medication be necessary.

5. An emergency burn package according to claim 4 in which flap opening contains cooperating Velco fasteners for maintaining each flap in a closed position when not in use.

6. An emergency burn treatment package according to claim 1 which includes a pair of fabric handles attached to the bottom portion of said flexible outer covering whereby the patient may be moved while in a flexible condition.

7. An emergency burn treatment package according to claim 1 in which each overlapping flexible outer covering is looped and stitched on the outer portion to define an opening running lengthwise of said foam material to define an opening for accepting a pole whereby said patient may be moved as on a litter.

8. An emergency burn treatment package for maintaining a patient in a sterile atmosphere comprising:
   a soft resilient foam material adapted to support a patient lying on said foam material,
   a sterile sheet on said foam material interspersed between said foam material and a patient lying on said foam material and adapted to completely cover and protect said patient from contamination, and
   a flexible outer covering having at least a pair of cooperating interlocking portions completely encompassing said foam material, patient and said sterile sheet for maintaining the sterile atmosphere about the patient.

9. An emergency burn treatment package according to claim 8 in which said pair of cooperating portions include a plurality of transverse Velco fasteners for interlocking said portions over a wide range of body sizes.

10. An emergency burn treatment package according to claim 8 in which each cooperating interlocking portion has a pair of flap openings for providing access to either hand or foot of the patient should external medication be necessary and in which each flap opening contains a Belco fastener for maintaining said flap in a closed position when not in use.

11. A method for providing emergency treatment to burn patients comprising the steps of:
   first placing a soft resilient material on a waterproof outer covering,
   then placing a closed sterile sheet on said soft resilient material,
   then place the patient on said sterile sheet,
   then open and cover the patient completely with the sterile sheet, and
   then enclose the patient with the waterproof material to thereby completely enclose and maintain the patient in a sterile atmosphere.

12. A method for providing emergency treatment to burn patients comprising the steps of:
   first placing a soft resilient water absorbent material on a waterproof outer covering,
   then placing a closed sterile sheet on said soft resilient material,
   then saturating the sterile sheet and soft resilient material with an aqueous solution,
   then placing a patient on said sterile sheet,
   then opening and covering the patient completely with the sterile sheet,
   then saturate the sterile sheet with an aqueous solution, and
   then enclose the patient with the waterproof outer material to thereby maintain the patient in a moist and sterile atmosphere.

* * * * *